United States Patent
Roth

(10) Patent No.: US 10,108,844 B2
(45) Date of Patent: *Oct. 23, 2018

(54) METHODS AND SYSTEMS FOR IMAGE DATA PROCESSING

(71) Applicant: Luminex Corporation, Austin, TX (US)

(72) Inventor: Wayne D. Roth, Leander, TX (US)

(73) Assignee: Luminex Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,546

(22) Filed: Sep. 18, 2017

(65) Prior Publication Data

US 2018/0018498 A1 Jan. 18, 2018

Related U.S. Application Data

(60) Continuation of application No. 15/069,037, filed on Mar. 14, 2016, now Pat. No. 9,767,344, which is a
(Continued)

(51) Int. Cl.
*G06K 9/00* (2006.01)
*G06T 7/194* (2017.01)
(Continued)

(52) U.S. Cl.
CPC ....... *G06K 9/0014* (2013.01); *G01N 15/1463* (2013.01); *G06T 7/0012* (2013.01);
(Continued)

(58) Field of Classification Search
CPC . G06T 2207/10064; G06T 2207/20021; G06T 2207/30024; G06T 2207/30072;
(Continued)

(56) References Cited

U.S. PATENT DOCUMENTS

| 5,107,422 A | 4/1992 | Kamentsky et al. |
| 5,162,990 A | 11/1992 | Odeyale et al. |

(Continued)

FOREIGN PATENT DOCUMENTS

| CN | 1474345 | 2/2004 |
| CN | 1556497 | 12/2004 |

(Continued)

OTHER PUBLICATIONS

Extended European Search Report in Application No. 17168644.7 dated Sep. 21, 2017, 8 pages.

(Continued)

*Primary Examiner* — Amara Abdi
(74) *Attorney, Agent, or Firm* — Meyertons, Hood, Kivlin, Kowert & Goetzel, P.C.

(57) ABSTRACT

Methods, storage mediums, and systems for image data processing are provided. Embodiments for the methods, storage mediums, and systems include configurations to perform one or more of the following steps: background signal measurement, particle identification using classification dye emission and cluster rejection, inter-image alignment, inter-image particle correlation, fluorescence integration of reporter emission, and image plane normalization.

20 Claims, 5 Drawing Sheets

Related U.S. Application Data division of application No. 14/257,630, filed on Apr. 21, 2014, now Pat. No. 9,286,504, which is a division of application No. 13/236,299, filed on Sep. 19, 2011, now Pat. No. 8,705,859, which is a division of application No. 11/534,166, filed on Sep. 21, 2006, now Pat. No. 8,031,918.

(60) Provisional application No. 60/719,010, filed on Sep. 21, 2005.

(51) Int. Cl.
*G06T 7/00* (2017.01)
*G01N 15/14* (2006.01)

(52) U.S. Cl.
CPC .... *G06T 7/194* (2017.01); *G06T 2207/10064* (2013.01); *G06T 2207/20021* (2013.01); *G06T 2207/30024* (2013.01); *G06T 2207/30072* (2013.01)

(58) Field of Classification Search
CPC ... G06T 7/0012; G06T 7/194; G01N 15/1463; G06K 9/0014
See application file for complete search history.

(56) References Cited

U.S. PATENT DOCUMENTS

| | | | |
|---|---|---|---|
| 5,206,699 A | 4/1993 | Stewart et al. | |
| 5,337,081 A | 8/1994 | Kamiya et al. | |
| 5,579,409 A | 11/1996 | Vaidyanathan et al. | |
| 5,623,560 A | 4/1997 | Nakajima et al. | |
| 5,715,334 A | 2/1998 | Peters | |
| 5,736,330 A | 4/1998 | Fulton | |
| 5,751,839 A * | 5/1998 | Drocourt | G01N 15/1468 250/461.2 |
| 5,828,766 A | 10/1998 | Gallo | |
| 5,836,872 A | 11/1998 | Kenet et al. | |
| 5,841,148 A | 11/1998 | Some et al. | |
| 5,981,180 A | 11/1999 | Chandler et al. | |
| 5,983,120 A * | 11/1999 | Groner | A61B 5/0261 356/364 |
| 6,057,107 A | 5/2000 | Fulton | |
| 6,165,734 A | 12/2000 | Garini et al. | |
| 6,268,222 B1 | 7/2001 | Chandler et al. | |
| 6,284,465 B1 | 9/2001 | Wolber | |
| 6,307,959 B1 | 10/2001 | Mandelbaum et al. | |
| 6,307,963 B1 | 10/2001 | Nishida et al. | |
| 6,417,501 B1 | 7/2002 | Yang et al. | |
| 6,449,562 B1 | 9/2002 | Chandler et al. | |
| 6,514,295 B1 | 2/2003 | Chandler et al. | |
| 6,524,793 B1 | 2/2003 | Chandler et al. | |
| 6,528,165 B2 | 3/2003 | Chandler | |
| 6,548,257 B2 | 4/2003 | Lockhart et al. | |
| 6,592,822 B1 | 7/2003 | Chandler | |
| 6,611,767 B1 | 8/2003 | Fiekowsky et al. | |
| 6,649,414 B1 | 11/2003 | Chandler et al. | |
| 6,687,395 B1 | 2/2004 | Dietz et al. | |
| 6,713,264 B2 | 3/2004 | Luttermann et al. | |
| 6,730,521 B1 | 5/2004 | Cassells | |
| 6,763,149 B2 * | 7/2004 | Riley | G01J 3/28 382/218 |
| 6,806,052 B2 | 10/2004 | Bridgham et al. | |
| 6,806,954 B2 | 10/2004 | Sandstrom | |
| 6,829,376 B2 * | 12/2004 | Bartell | G06T 7/73 382/128 |
| 6,876,760 B1 | 4/2005 | Vaisberg et al. | |
| 6,885,440 B2 | 4/2005 | Silcott et al. | |
| 6,903,207 B2 | 6/2005 | Mirkin et al. | |
| 6,939,720 B2 | 9/2005 | Chandler et al. | |
| 7,236,620 B1 | 6/2007 | Gurcan | |
| 8,031,918 B2 | 10/2011 | Roth | |
| 8,542,897 B2 | 9/2013 | Roth | |

| | | | |
|---|---|---|---|
| 2001/0041347 A1 | 11/2001 | Sammak et al. | |
| 2002/0141631 A1 | 10/2002 | Vaisberg et al. | |
| 2002/0164063 A1 | 11/2002 | Heckman | |
| 2002/0176606 A1 | 11/2002 | Wernet et al. | |
| 2003/0016860 A1 | 1/2003 | Sugawara | |
| 2003/0036067 A1 | 2/2003 | Schwartz | |
| 2003/0096322 A1 | 5/2003 | Giuliano et al. | |
| 2003/0138140 A1 | 7/2003 | Marcelpoil et al. | |
| 2003/0198385 A1 * | 10/2003 | Tanner | G06K 9/00 382/195 |
| 2003/0218137 A1 | 11/2003 | Sendai | |
| 2004/0071328 A1 | 4/2004 | Vaisberg | |
| 2004/0095611 A1 | 5/2004 | Watanabe et al. | |
| 2005/0009032 A1 | 1/2005 | Coleman et al. | |
| 2005/0078881 A1 | 4/2005 | Xu et al. | |
| 2006/0013454 A1 * | 1/2006 | Flewelling | A61B 1/042 382/128 |
| 2006/0014137 A1 | 1/2006 | Ghosh et al. | |
| 2006/0045388 A1 * | 3/2006 | Zeineh | G02B 21/365 382/312 |
| 2006/0105395 A1 | 5/2006 | Pempsell | |
| 2008/0111086 A1 | 5/2008 | Betzig et al. | |
| 2011/0045993 A1 | 2/2011 | Kent et al. | |
| 2011/0316998 A1 | 12/2011 | Kishima | |

FOREIGN PATENT DOCUMENTS

| | | |
|---|---|---|
| CN | 1632831 | 6/2005 |
| EP | 0421736 | 4/1991 |
| EP | 1439384 | 7/2004 |
| EP | 1929274 | 6/2008 |
| JP | 7-264483 | 10/1995 |
| JP | 8-304288 | 11/1996 |
| JP | 2000299874 | 10/2000 |
| JP | 2002344978 | 11/2002 |
| JP | 2003262588 | 9/2003 |
| JP | 2005127790 | 5/2005 |
| JP | 2005527827 | 9/2005 |
| WO | 00/29984 | 5/2000 |
| WO | 01/11340 | 2/2001 |
| WO | 2003/069421 | 8/2003 |
| WO | 2003100474 | 12/2003 |
| WO | 2004036162 | 4/2004 |
| WO | 2004-055505 | 7/2004 |
| WO | 2005001436 | 1/2005 |
| WO | 2007035840 | 3/2007 |

OTHER PUBLICATIONS

Office Action in India Application No. 359/MUMNP/2008 dated Jul. 25, 2013, 4 pages.
Office Action in Japanese Patent Application No. 2012-000148 dated Dec. 3, 2013, 4 pages.
Office Action in Japanese Patent Application No. 2012-000148 dated Jan. 4, 2013, 6 pages.
Office Action in Chinese Application No. 201210021093.7 dated Dec. 11, 2013, 12 pages.
Office Action in Korean Patent Application No. 10-2008-7009141 dated Aug. 20, 2012, 7 pages.
Office Action in Chinese Patent Application No. 200680034792.8 dated Sep. 26, 2011, 5 pages.
Office Action in Japanese Patent Application No. 2008-532362 dated Oct. 4, 2011, 3 pages.
Office Communication in European Patent Application No. 06 803 948.6 dated Jan. 21, 2011, 6 pages.
International Search Report in Application No. PCT/US2006/036733 dated Aug. 20, 2007, 6 pages.
Statistical Algorithms Description Document, Affymetrix, Inc., 2002, pp. 1-28.
Paul Pempsell, "Methods and Systems for Positioning Microspheres for Imaging," U.S. Appl. No. 11/270,786, filed Nov. 9, 2005, 27 pages.
Office Action in U.S. Appl. No. 11/534,166 dated Dec. 10, 2009, 16 pages.
Office Action in U.S. Appl. No. 11/534,166 dated Jul. 28, 2010, 19 pages.

(56) References Cited

OTHER PUBLICATIONS

Office Action in U.S. Appl. No. 11/534,166 dated Nov. 17, 2010, 16 pages.
Office Action in U.S. Appl. No. 13/236,299 dated Dec. 4, 2012, 8 pages.
Office Action in U.S. Appl. No. 13/236,299 dated Jul. 15, 2013, 10 pages.
Office Action in U.S. App. No. 14/257,630 dated Jul. 16, 2015, 19 pages.
Office Action in Canadian Application No. 2,623,130 dated May 15, 2014, 3 pages.
Office Action in Canadian Application No. 2,623,130 dated Jun. 4, 2015, 4 pages.
Second Office Action in Chinese Application No. 201210021100.3 dated Aug. 13, 2014, 9 pages.
Third Office Action in Chinese Application No. 201210021100.3 dated Feb. 25, 2015, 12 pages.
Second Office Action in Chinese Application No. 201210021093.7 dated Jul. 21, 2014, 10 pages.
Office Action in European Application No. 06803948.6 dated Nov. 26, 2014, 4 pages.
Extended European Search Report Patent Application No. 10183403.4 dated Aug. 25, 2011, 7 pages.
Office Action in Indian Patent Application No. 359/MUMNP/2008 dated Apr. 9, 2015, 2 pages.
Office Action in Canadian Application No. 2,623,130 dated Aug. 25, 2016, 3 pages.
Office Action in U.S. Appl. No. 15/069,037 dated Nov. 28, 2016, 21 pages.

\* cited by examiner

METHODS AND SYSTEMS FOR IMAGE DATA PROCESSING

PRIORITY CLAIM

The present application is a continuation of U.S. application Ser. No. 15/069,037, filed Mar. 14, 2016 (now U.S. Pat. No. 9,767,344), which is a divisional of U.S. application Ser. No. 14/257,630, filed Apr. 21, 2014 (now U.S. Pat. No. 9,286,504), which is a divisional of U.S. application Ser. No. 13/236,299, filed Sep. 19, 2011 (now U.S. Pat. No. 8,705,859), which is a divisional of U.S. application Ser. No. 11/534,166, filed Sep. 21, 2006 (now U.S. Pat. No. 8,031,918), which claims priority to U.S. Provisional Appl. No. 60/719,010, filed Sep. 21, 2005; the disclosures of each of the above-referenced applications are incorporated by reference herein in their entireties.

BACKGROUND OF THE INVENTION

1. Field of the Invention

This invention generally relates to methods and systems for image data processing. Certain embodiments relate to methods and systems for performing one or more steps for processing images of particles for multiplexed applications.

2. Description of the Related Art

The following descriptions and examples are not admitted to be prior art by virtue of their inclusion within this section.

Imaging using detectors such as charged coupled device (CCD) detectors is employed in several currently available instruments in biotechnology applications. Many of the commercially available systems are configured to image target human (or other animal) cells. Such systems, however, are not utilized to generate images using different wavelengths of light for determining the identity of or subset to which the cells belong. For multiplexed applications in which CCD detectors are used to measure fluorescent emission of cells, the subset or class of cells or other particles is based on the absolute position of the fluorescence emission within the image rather than the characteristics of the fluorescence emission such as wavelength composition.

Accordingly, it would be desirable to develop methods and systems for data processing of images of particles for multiplexed applications.

SUMMARY OF THE INVENTION

The problems outlined above may be in large part addressed by computer-implemented methods, storage mediums, and systems for performing one or more steps associated with data image processing of particles. The following are mere exemplary embodiments of the computer-implemented methods, storage mediums, and systems and are not to be construed in any way to limit the subject matter of the claims.

Embodiments of the computer-implemented methods, storage mediums, and systems may be configured to separate an image of particles having fluorescence-material associated therewith into an array of subsections, determine a statistical value of an optical parameter measured for a plurality of pixels within a subsection, and assign the determined statistical value as background signal for the corresponding subsection.

Other embodiments of the computer-implemented methods, storage mediums, and systems may additionally or alternatively be configured to analyze an image of particles having fluorescence-material associated therewith to identify one or more pixels within the image that exhibit an optical parameter value above a first predetermined threshold. In addition, the methods, storage mediums, and systems may be configured to determine locations within sets of the one or more identified pixels that respectively exhibit maximum values for the optical parameter within the sets and compute a rate of intensity change of the optical parameter for a plurality of pixels surrounding at least one of the locations.

Other embodiments of the computer-implemented methods, storage mediums, and systems may additionally or alternatively be configured to acquire data for multiple images of the particles, wherein each of the multiple images corresponds to a different wavelength band. Moreover, the methods, storage mediums, and systems may be configured to create a composite image of the multiple images and manipulate the coordinates of at least one of the multiple images such that spots corresponding to the particles within each of the multiple images converge within an ensuing composite image.

Yet other embodiments of the computer-implemented methods, storage mediums, and systems may additionally or alternatively be configured to analyze a first image of particles having a uniform concentration of fluorescence-material associated therewith and a second image of particles having an unknown concentration of fluorescence-material associated therewith to respectively identify one or more pixels within the first and second images that exhibit an optical parameter value above a first predetermined threshold. In addition, the methods, storage mediums, and systems may be configured to categorize, within respective subsections of the first and second images, collections of pixels respectively identified during the step of analyzing the first and second images, wherein dimensions of the subsections in the first and second images are substantially equal. The methods, storage mediums, and systems may also be configured to develop for each respective subsection within the first image a statistic representative of the fluorescence emission level of the collections of pixels categorized thereto. Moreover, the methods, storage mediums, and systems may be configured to divide the fluorescence emission level of each collection of pixels identified during the step of analyzing the second image by the statistic developed for the corresponding first image subsection to obtain a normalized value of fluorescence.

BRIEF DESCRIPTION OF THE DRAWINGS

Other objects and advantages of the invention will become apparent upon reading the following detailed description and upon reference to the accompanying drawings in which.

Figure 1:
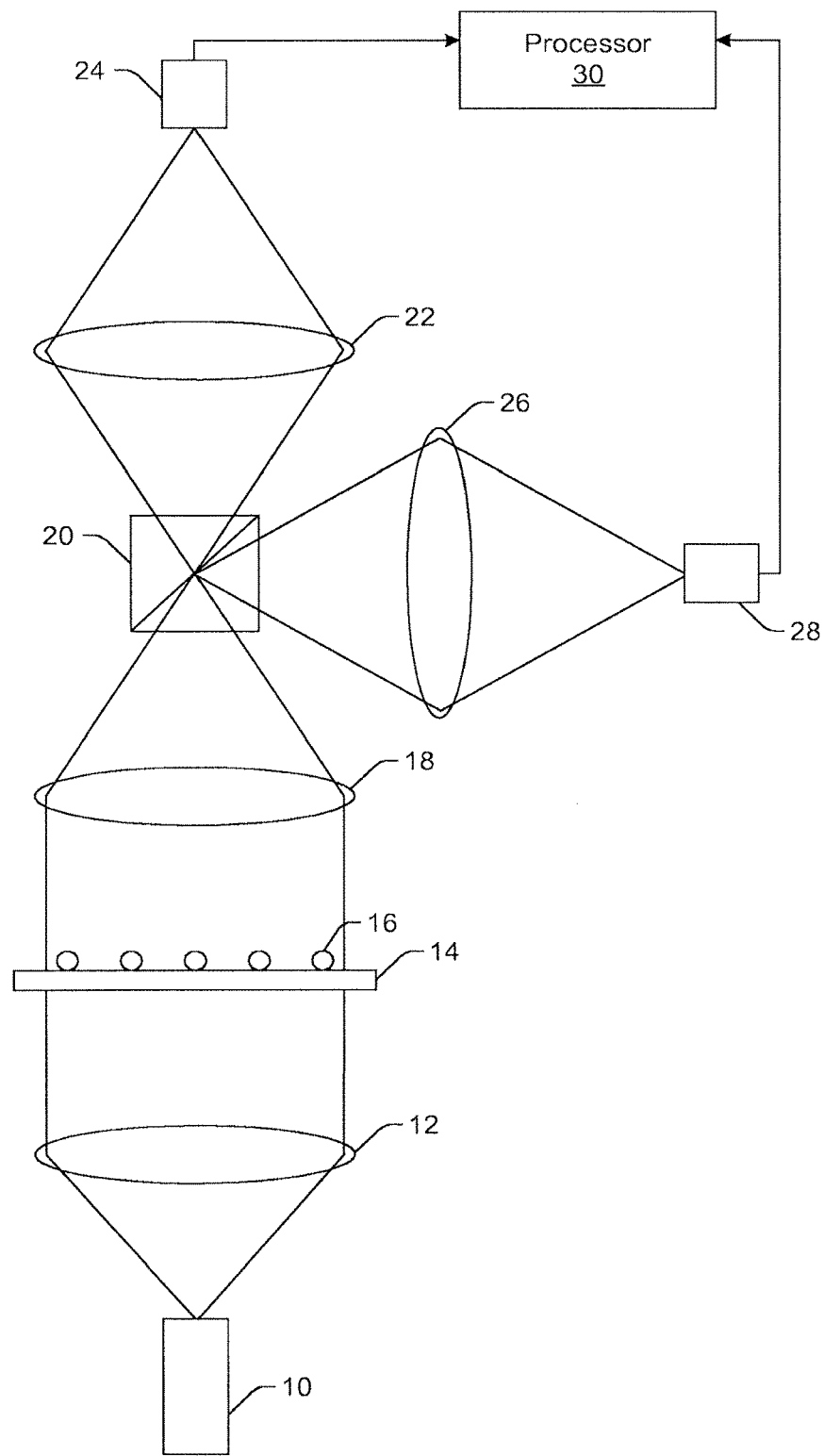
FIG. 1 is a schematic diagram illustrating a cross-sectional view of one embodiment of a system configured to acquire and process images for multiplexed applications.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated and described in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation of Austin, Tex. The terms "particles" and "microspheres" are used interchangeably herein.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated and described in U.S. Pat. No. 6,268,222 to Chandler et al. and U.S. Pat. No. 6,649,414 to Chandler et al., which are incorporated by reference as if fully set forth herein. The types of particles that can be used in the methods and systems described herein also include particles having one or more fluorochromes or fluorescent dyes incorporated into the core of the particles.

Particles that can be used in the methods and systems described herein further include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles. As described below, image data processing may include classification of the particles, particularly for a multi-analyte fluid, as well as a determination of the amount of analyte bound to the particles. Since a reporter signal, which represents the amount of analyte bound to the particle, is typically unknown during operations, specially dyed particles, which not only emit fluorescence in the classification wavelength(s) or wavelength band(s) but also in the reporter wavelength or wavelength band, may be used for the processes described herein.

The methods described herein generally include analyzing one or more images of particles and processing data measured from the images to determine one or more characteristics of the particles, such as but not limited to numerical values representing the magnitude of fluorescence emission of the particles at multiple detection wavelengths. Subsequent processing of the one or more characteristics of the particles, such as using one or more of the numerical values to determine a token ID representing the multiplex subset to which the particles belong and/or a reporter value representing a presence and/or a quantity of analyte bound to the surface of the particles, can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, and U.S. Pat. No. 6,939,720 to Chandler et al., which are incorporated by reference as if fully set forth herein. In one example, techniques described in U.S. Pat. No. 5,981,180 to Chandler et al. may be used with the fluorescent measurements described herein in a multiplexing scheme in which the particles are classified into subsets for analysis of multiple analytes in a single sample.

Turning now to the drawings, it is noted that FIG. 1 is not drawn to scale. In particular, the scale of some of the elements of the figure is greatly exaggerated to emphasize characteristics of the elements. Some elements of the system have not been included in the figures for the sake of clarity.

One embodiment of a system configured to generate, acquire, or supply images of particles and to process the images according to embodiments of methods described herein is shown in FIG. 1. The system shown in FIG. 1 may be used in applications such as multi-analyte measurement of particles. The system includes an imaging subsystem that includes light source 10. Light source 10 may include one or more light sources such as light emitting diodes (LED), lasers, arc lamps, incandescent lamps, or any other suitable light sources known in the art. In addition, or alternatively, the light source may include more than one light source (not shown), each of which is configured to generate light a different wavelength or a different wavelength band. One example of an appropriate combination of light sources for use in the system shown in FIG. 1 includes, but is not limited to, two or more LEDs. Light from more than one light source may be combined into a common illumination path by a beam splitter (not shown) or any other suitable optical element known in the art such that light from the light sources may be directed to the particles simultaneously. Alternatively, the imaging subsystem may include an optical element (not shown) such as a reflecting mirror and a device (not shown) configured to move the optical element into and out of the illumination path depending on which light source is used to illuminate the particles. In this manner, the light sources may be used to sequentially illuminate the particles with different wavelengths or wavelength bands of light. The light source(s) may also illuminate the substrate from above, rather than below the substrate (not shown).

The light source(s) may be selected to provide light at wavelength(s) or wavelength band(s) that will cause the particles or material coupled thereto to emit fluorescence. For instance, the wavelength(s) or wavelength band(s) may be selected to excite fluorescent dyes or other fluorescent materials incorporated into the particles and/or coupled to a surface of the particles. In this manner, the wavelength(s) or wavelength band(s) may be selected such that the particles emit fluorescence that is used for classification of the particles. In addition, the wavelength(s) or wavelength band(s) may be selected to excite fluorescent dyes or other fluorescent materials coupled to the particles via a reagent on the surface of the particles. As such, the wavelength(s) or wavelength band(s) may be selected such that the particles emit fluorescence that is used to detect and/or quantify reaction(s) that have taken place on the surface of the particles.

As shown in FIG. 1, the imaging subsystem may include optical element 12 that is configured to direct light from light source 10 to substrate 14 on which particles 16 are immobilized. In one example, optical element 12 may be a collimating lens. However, optical element 12 may include any other appropriate optical element that can be used to image light from light source 10 onto substrate 14. In addition, although the optical element is shown in FIG. 1 as a single optical element, it is to be understood that optical element 12 may include more than one refractive element. Furthermore, although optical element 12 is shown in FIG. 1 as a refractive optical element, it is to be understood that one or more reflective optical elements may be used (possibly in combination with one or more refractive optical elements) to image light from light source 10 onto substrate 14.

Particles 16 may include any of the particles described above. Substrate 14 may include any appropriate substrate known in the art. The particles immobilized on substrate 14 may be disposed in an imaging chamber (not shown) or any other device for maintaining a position of substrate 14 and particles 16 immobilized thereon with respect to the imaging subsystem. The device for maintaining a position of substrate 14 may also be configured to alter a position of the substrate (e.g., to focus the imaging subsystem onto the substrate) prior to imaging. Immobilization of the particles on the substrate may be performed using magnetic attraction, a vacuum filter plate, or any other appropriate method known in the art. Examples of methods and systems for positioning microspheres for imaging are illustrated in U.S. patent application Ser. No. 11/270,786 to Pempsell filed Nov. 9, 2005, which is incorporated by reference as if fully set forth herein. The particle immobilization method itself is not particularly important to the method and systems described herein. However, the particles are preferably immobilized such that the particles do no move perceptibly during the detector integration period, which may be multiple seconds long.

As shown in FIG. 1, the imaging subsystem may include optical element 18 and beam splitter 20. Optical element 18 is configured to focus light from substrate 14 and particles 16 immobilized thereon to beam splitter 20. Optical element 18 may be further configured as described above with respect to optical element 12. Beam splitter 20 may include any appropriate beam splitter known in the art. Beam splitter 20 may be configured to direct light from optical element 18 to different detectors based on the wavelength of the light. For example, light having a first wavelength or wavelength band may be transmitted by beam splitter 20, and light having a second wavelength or wavelength band different than the first may be reflected by beam splitter 20. The imaging subsystem may also include optical element 22 and detector 24. Light transmitted by beam splitter 20 may be directed to optical element 22. Optical element 22 is configured to focus the light transmitted by the beam splitter onto detector 24. The imaging subsystem may further include optical element 26 and detector 28. Light reflected by beam splitter 20 may be directed to optical element 26. Optical element 26 is configured to focus the light reflected by the beam splitter onto detector 28. Optical elements 22 and 26 may be configured as described above with respect to optical element 12.

Detectors 24 and 28 may include, for example, charge coupled device (CCD) detectors or any other suitable imaging detectors known in the art such as CMOS detectors, two-dimensional arrays of photosensitive elements, time delay integration (TDI) detectors, etc. In some embodiments, a detector such as a two-dimensional CCD imaging array may be used to acquire an image of substantially an entire substrate or of all particles immobilized on a substrate simultaneously. In this manner, all photons from the illuminated area of the substrate may be collected simultaneously thereby eliminating error due to a sampling aperture used in other currently available systems that include a photomultiplier tube (PMT) and scanning device. In addition, the number of detectors included in the system may be equal to the number of wavelengths or wavelength bands of interest such that each detector is used to generate images at one of the wavelengths or wavelength bands.

Each of the images generated by the detectors may be spectrally filtered using an optical bandpass element (not shown) or any other suitable optical element known in the art, which is disposed in the light path from the beam splitter to the detectors. A different filter "band" may be used for each captured image. The detection wavelength center and width for each wavelength or wavelength band at which an image is acquired may be matched to the fluorescent emission of interest, whether it is used for particle classification or the reporter signal. In this manner, the imaging subsystem of the system shown in FIG. 1 is configured to generate multiple images at different wavelengths or wavelength bands simultaneously. Although the system shown in FIG. 1 includes two detectors, it is to be understood that the system may include more than two detectors (e.g., three detectors, four detectors, etc.). As described above, each of the detectors may be configured to generate images at different wavelengths or wavelength bands simultaneously by including one or more optical elements for directing light at different wavelengths or wavelength bands to the different detectors simultaneously.

In addition, although the system is shown in FIG. 1 to include multiple detectors, it is to be understood that the system may include a single detector. The single detector may be used to generate multiple images at multiple wavelengths or wavelength bands sequentially. For example, light of different wavelengths or wavelength bands may be directed to the substrate sequentially, and different images may be generated during illumination of the substrate with each of the different wavelengths or wavelength bands. In another example, different filters for selecting the wavelength or wavelength bands of light directed to the single detector may be altered (e.g., by moving the different filters into and out of the imaging path) to generate images at different wavelengths or wavelength bands sequentially.

The imaging subsystem shown in FIG. 1, therefore, is configured to generate a plurality or series of images representing the fluorescent emission of particles 16 at several wavelengths of interest. In addition, the system may be configured to supply a plurality or series of digital images representing the fluorescence emission of the particles to a processor (i.e., a processing engine). In one such example, the system may include processor 30. Processor 30 may be configured to acquire (e.g., receive) image data from detectors 24 and 28. For example, processor 30 may be coupled to detectors 24 and 28 in any suitable manner known in the art (e.g., via transmission media (not shown), each coupling one of the detectors to the processor, via one or more electronic components (not shown) such as analog-to-digital converters, each coupled between one of the detectors and the processor, etc.). Preferably, processor 30 is configured to process and analyze these images to determine one or more characteristics of particles 16 such as a classification of the particles and information about a reaction taken place on the surface of the particles. The one or more characteristics may be output by the processor in any suitable format such as a data array with an entry for fluorescent magnitude for each particle for each wavelength. Specifically, the processor may be configured to perform one or more steps of the method embodiments described herein to process and analyze the images.

Processor 30 may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions (not shown) executable on processor 30 to perform one or more steps of the computer-implemented methods described herein may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others.

Program instructions implementing methods such as those described herein may be transmitted over or stored on a storage medium. The storage medium may include but is not limited to a read-only memory, a random access memory, a magnetic or optical disk, or a magnetic tape. For each image, all located particles and the values and/or statistics determined for each identified particle may be stored in a memory medium within the storage medium. The image processing methods described herein may be performed using one or more algorithms. As described in more detail below, the algorithms may be complex and, therefore, may be best implemented through a computer. As such, the methods described herein and particularly in reference to FIGS. 2-5 may be referred to as "computer-implemented methods" and, thus, the terms "method" and "computer-implements method" may be used interchangeably herein. It is noted that the computer-implemented methods and program instructions of the systems described herein may, in some cases, be configured to perform processes other than those associated with methods described herein and, therefore, the computer-implemented methods and program instructions of systems described herein are not necessarily limited to the depiction of FIGS. 2-5.

The imaging based systems described herein are viable candidates to replace traditional flow cytometry type measurement systems. The methods, storage mediums, and systems described herein may be more complex in a data processing sense than that which is necessary for flow cytometry based applications. However, the hardware of the systems described herein (e.g., the light source, optical elements, detectors, etc.) has the potential to be significantly less expensive and more robust than that of typical flow cytometers. It is expected that further evaluation and improvement of the methods described herein (e.g., further evaluation and improvement of algorithms that may be used to implement the methods) will lead to a reduced need for processing power and more accurate determination of fluorescent emission values and, therefore, more accurate determination of one or more characteristics of the particles.

According to one embodiment, a computer-implemented method for image data processing includes one or more of the following steps (i.e., high level operations): background signal measurement, particle identification (i.e., discovery) using classification dye emission and cluster rejection, inter-image alignment, inter-image particle correlation, fluorescence integration of reporter emission, and image plane normalization. These steps may be performed sequentially in the order listed above.

Figure 2:
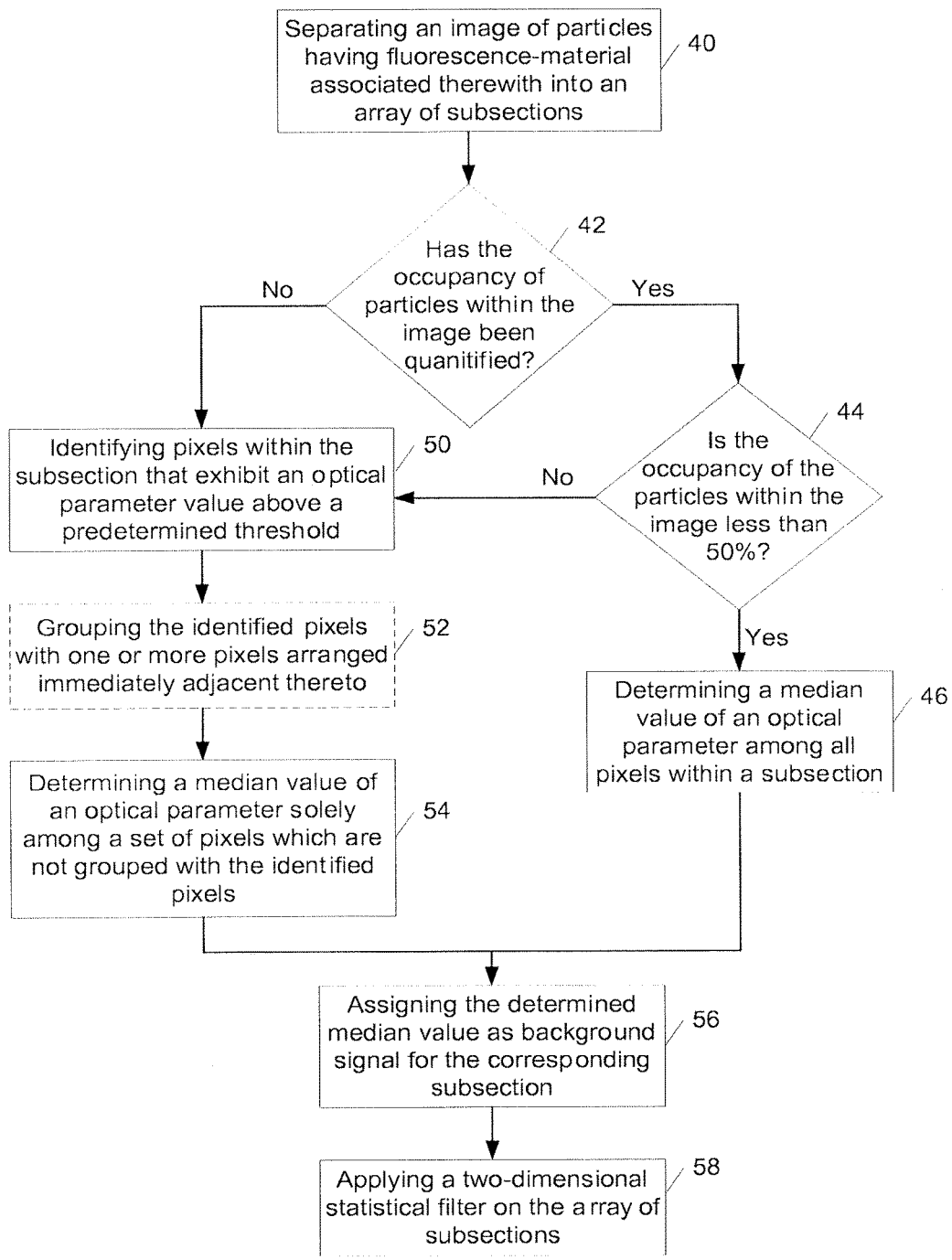
FIG. 2 is a flowchart outlining a method for determining background signals within an image.

In general, background signal measurement may be performed such that the fluorescence emitted from a particle may be accurately determined (i.e., the measurement of fluorescence from a particle may be determined irrespective of the level of reflective light in the background of the image as well as noise and dark current offset from the imaging system used to image the particle). FIG. 2 illustrates a flowchart illustrating an exemplary sequence of steps for measuring the background signal of an image. As shown in block 40 of FIG. 2, the method may include separating an image of particles having fluorescence-material associated therewith into an array of subsections. Such an array may include any number of rows and columns, depending on the clarity of desired background signal, the processing capability of the system, and/or the number of particles being analyzed. As further shown in FIG. 2, the route the method continues along after block 40 may depend on the occupancy of the particles within the image. In particular, after block 40, the flowchart continues to block 42 in which a determination is made as to whether the occupancy of the particles within the image has been quantified.

In embodiments in which the occupancy of particles has been quantified, the method may continue to block 44 in which a determination of whether the occupancy is less than a predetermined threshold. The flowchart in FIG. 2 specifically notes a threshold of 50% occupancy within block 44, but it is noted that the method is not necessarily so limited. In particular, the method may be modified to consider any predetermined quantity of occupancy by which to determine the course of action for measuring the background signal of an image. In embodiments in which particles of interest occupy less than a predetermined threshold (e.g., less than about 50%) of the imaging area, background signal measurement may include determining a statistical value of an optical parameter among all pixels within a subsection as noted in block 46. Consequently, fluorescence values of the relatively bright pixels corresponding to particles within the subsection may be merged with signals from background pixels (pixels which do not correspond to the presence of pixels) within the subsection. Since the particles occupy a smaller amount of the subsection, however, the statistical value may be more representative of the background pixels. In general, the statistical value may include any number of statistical parameters, including but not limited to median, mean, mode, and trimmed mean. In some embodiments, determining a median value may be particularly advantageous.

In other embodiments, the method may continue to blocks 50, 52, and 54 to determine a statistical value of an optical parameter of less than all of the pixels within a subsection. In particular, in embodiments in which the occupancy of particles of interest is greater than or equal to a predetermined threshold of the imaging area (e.g., greater than or equal to about 50% as noted by the arrow connecting block 44 to block 50) or when the occupancy of the imaging area by the particles is unknown (e.g., as noted by the arrow connecting block 42 to block 50), the method for background signal measurement may compensate for the larger or unknown ratio of particle area to background area by determining a statistical value of an optical parameter of less than all of the pixels within a subsection. In particular, pixels within an image exhibiting an optical parameter value above a predetermined threshold may be identified as noted in block 50. In some cases, the pixels identified in block 50 may be grouped with pixels arranged immediately adjacent thereto as noted in block 52. Such a process step, however, is optional as denoted by the dotted line border of the block and, therefore, may be omitted from the method in some cases.

In any case, the method may continue to block 54 in which a statistical value of an optical parameter is determined solely among a set of pixels within the subsection which are not identified to exhibit an optical parameter above the predetermined threshold outlined in block 50. In some embodiments, pixels grouped with such identified pixels may also be excluded from the determination of the statistical value of the optical parameter. In this manner, pixels identified in block 50 and, in some cases, the pixels grouped with the identified pixels in block 52 may be isolated from the measurement of the background signal.

In any case, regardless of the sequence of process steps used, the optical parameter of which a statistical value is determined may be any fluorescence emission of the particle measured at one or more detection wavelengths, emissions of scattered light in the background of the image as well as any noise and dark current offset from the imaging system used to image the particle. In addition, regardless of the sequence of process steps used, the method may continue to block 56 to assign the determined statistical value as background signal for the corresponding subsection. More specifically, the background signal level for all pixels within a subsection may be assigned the statistical value computed for the subsection. In some cases, the process steps of blocks 46, 50, 52, 54, and 56 may be repeated for other subsections in the image and, in some cases, for all subsections in the image. In this manner, a statistical value of an optical parameter may be determined for each of a plurality of subsections and, in some cases, for all of the subsections. In some cases, a relatively sharp contrast in statistical values may be present at the boundary between two subsections. In order to smooth the discontinuous difference in the statistical values between adjacent subsections, a two-dimensional statistical filter (e.g., a median filter or a mean filter) may be performed on the array of subsections. As a result, the subsections may be smoothed at their edges. Regardless of whether such a statistical filter is used, a resultant n×m matrix of subsections of pixels containing the computed statistical values may be saved as a "background image," which may be utilized as described further herein.

It is noted that the method described in reference to FIG. 2 may include additional steps of the above-described method for background signal measurement and, therefore, the method is not necessarily limited by the depiction of FIG. 2. For example, the omission of a reiteration of blocks 46, 50, 52, 54, and 56 in FIG. 2 does not necessarily limit the inclusion of such a possibility for the method described herein. As noted above, the method described herein for image data processing may include a process of particle discovery using fluorescence emission from the classification dye(s) and cluster rejection (i.e., rejection of particles that are located relatively close together). In some embodiments, the process of particle discovery described herein may be performed subsequent to the determination of a level of background signal within an image and, in some cases, may be specifically performed subsequent to the method of background signal measurement described in reference to FIG. 2. In other embodiments, however, the process of particle discovery described herein may be performed independent of background signal measurements.

Figure 3:
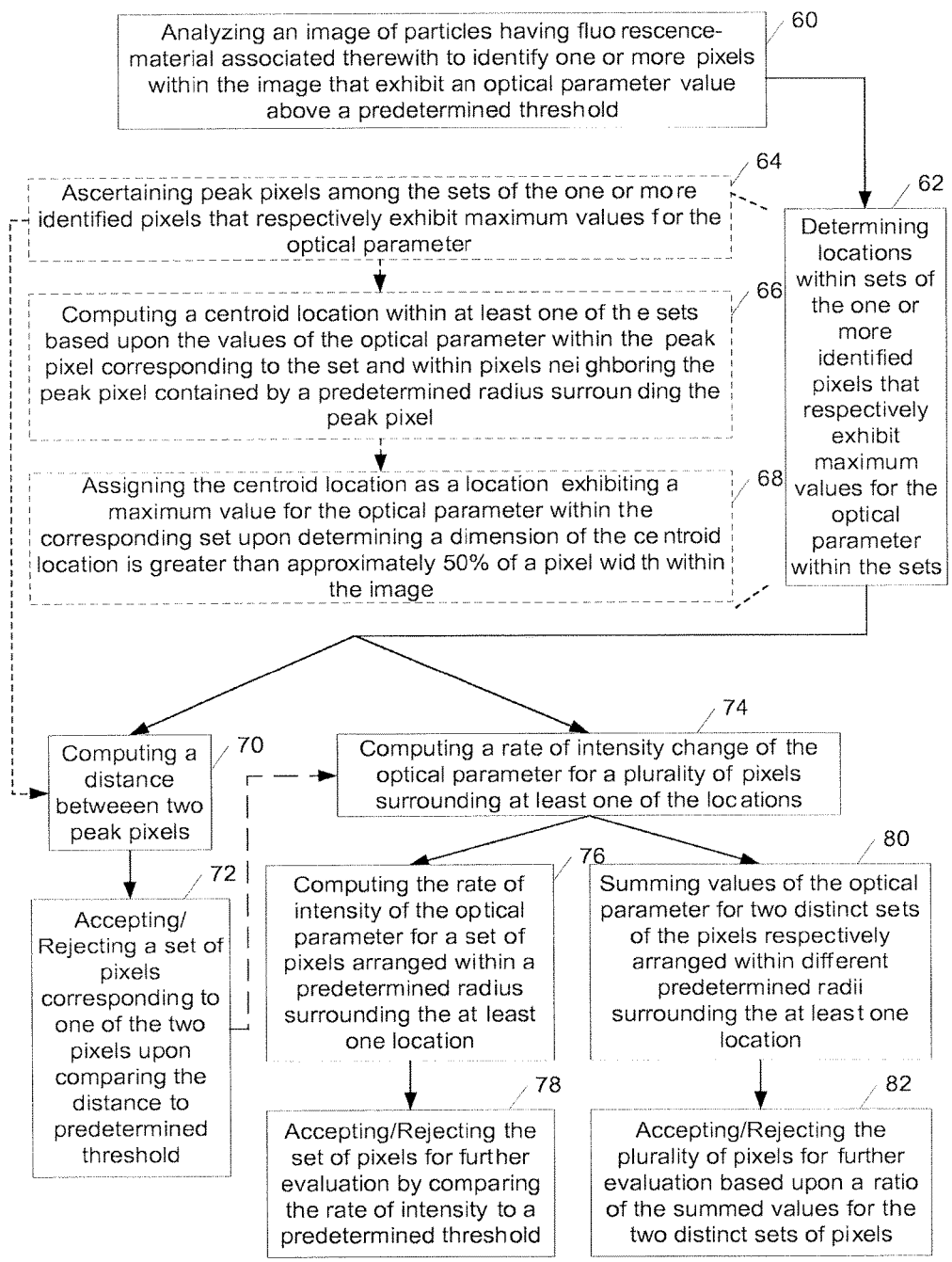
FIG. 3 is a flowchart outlining a method of particle discovery and determination of particle acceptance or rejection for further imaging processing.

FIG. 3 illustrates a flowchart illustrating an exemplary sequence of steps for a process of particle discovery. As shown in block 60 of FIG. 3, the method may include analyzing an image of particles having fluorescence-material associated therewith to identify one or more pixels within the image that exhibit an optical parameter value above a predetermined threshold. For example, a classification image (i.e., an image generated from light emitted at a wavelength or wavelength band of a classification dye) may be searched for pixels that exhibit fluorescence higher in intensity than the background signal of the image. In some embodiments, the image may be searched for pixels significantly higher in intensity than the background signal of the image, such as on the order of 2 to 1000 times higher in intensity. Smaller or larger intensity levels relative to the background signal of the image may also be used. In other cases, the image may be searched for pixels exhibiting a fixed value of fluorescence, which may or may not be dependent on the background signal of the image. In any case, a higher level of fluorescence emission by a pixel or a collection of pixels may indicate the presence of a fluorescence emitting particle. In some embodiments, the particle may be contained within a single pixel. In other embodiments, however, the particle may spread across a plurality of pixels.

In any case, the pixels identified in block 60 may be evaluated to determine the location of particles within the image. In particular, the method outlined in FIG. 3 may continue to block 62 to determine locations within sets of one or more identified pixels that respectively exhibit a maximum value for the optical parameter to detect the presence of particles within the image. Although the pixels may be evaluated individually and, therefore, a location within a single pixel may be determined by block 62, block 62 may also include determining a location among a collection of identified pixels. As used herein, a "collection of pixels" may generally refer to a grouping of pixels which are arranged immediately adjacent to each other (i.e., a cluster or conglomerate of contiguously arranged pixels).

In some embodiments, it may be advantageous to evaluate a collection of pixels for determining locations of particles within an image. In particular, as noted above, a particle may spread across a plurality of pixels and, as such, determining locations within individual pixels may falsely convey the presence of more particles than are actually imaged. Furthermore, if a particle is located relatively close to one or more other particles in an image, the fluorescence of the particles may affect the evaluation of each other's characteristics. Consequently, data for the particles may not be accurately determined. In some cases, a collection of pixels may be rejected (e.g., eliminated from any further image processing) if it is determined the characteristics of an encompassed particle cannot be accurately evaluated. Exemplary manners in which to determine whether a collection of pixels may be accepted or rejected for further image processing are described in more detail below in reference to blocks 70-78 of FIG. 3.

In general, the process outlined in block 62 for determining locations within sets of one of more identified pixels may be conducted in a number of different manners. Some exemplary methods are outlined in blocks 64, 66, and 68 in FIG. 3 (blocks 64, 66, and 68 extend from block 62 by dotted lines and are bordered by dotted lines, indicating the processes are exemplary). As shown in FIG. 3, block 64 outlines a process for ascertaining peak pixels among the sets of one or more identified pixels that respectively exhibit maximum values for the optical parameter. In such a process, each set of pixels may be iterated through to determine if the fluorescence value measured for each pixel has the maximum value within the set of pixels. The pixel with the maximum value may be ascertained as the "peak pixel". In some cases, a central portion of the peak pixel may be designated as the location. In such cases, the process of determining the location as outlined in block 62 may be simply conducted by the process outlined in block 64.

In some embodiments, however, it may be advantageous to determine if an alternative portion of the peak pixel is more suitable for the location exhibiting the maximum value for the optical parameter. For instance, particles may not be perfectly aligned among the pixels of the image and, consequently, the energy from a particle may not be evenly distributed among a set of identified pixels. In such cases, a central portion of a peak pixel may not be representative of the maximum fluorescence measurement for the particle and, therefore, it may be advantageous to determine if an off-center portion of the peak pixel may better represent the maximum fluorescence measurement for the particle. In such cases, the method may continue to block 66 to compute a centroid location within at least one of the sets of one or more identified pixels that exhibits a maximum value for the optical parameter. In particular, the method may include integrating fluorescence measurements of pixels adjacent to and within a predetermined radius of a peak pixel. An exemplary radius from the peak pixel may be selected from a range of 1 to 10 pixels, but other radii may be considered. It is noted that in embodiments in which the predetermined radius encompasses pixels which have not been identified to have an optical parameter above a predetermined threshold, the background signal all of such "background pixels" may be subtracted from this integral.

In some cases, it may be advantageous to analyze whether to assign the computed centroid location as the location exhibiting a maximum value for the optical parameter. As such, in some embodiments, the method may, in some embodiments, continue to block 68 depending on the characteristics of the computed centroid location. For example, if the centroid location is greater than one half of a pixel width in any direction, the computed location rounded up to the next integer value (e.g., in x and y coordinates) may be assigned as the location exhibiting a maximum value for the optical parameter. Although block 68 specifies a dimensional threshold for the computed centroid location to be greater than 50% of the dimensions of the pixels to assign the centroid location, the contingency process is not necessarily so limited. In particular, any dimensional threshold for the centroid location (including those which are independent of the pixel dimensions) may be used to determine whether to assign the centroid location.

Subsequent to the process for determining the locations exhibiting a maximum value for the optical parameter, the method may continue to processes for accepting and rejecting pixels for further image processing. For example, the method may, in some embodiments, continue to block 70 in which a distance between two peak pixels is computed. The identification of the peak pixels may generally be performed by the process described above in reference to block 64 and, therefore, the flowchart in FIG. 3 includes a dotted line connecting blocks 64 and 70 to indicate the correlation. Based upon the distance computed in block 70, a set of pixels corresponding to one of the two peak pixels may be accepted or rejected for further image processing as noted in block 72. For example, a set of pixels corresponding to one of the two peak pixels may be rejected for further image processing if the distance between the peak pixels is less than (and/or equal to) a predetermined threshold, such as but not limited to a threshold equivalent to projected diameters of one or two imaged particles or any distance therebetween. In this manner, fluorescence emissions of particles which are arranged too close to a particle of interest, which may hinder the evaluation of the particle of interest, may be averted.

In general, the term "projected diameter of an imaged particle," as used herein, may refer to an estimated diameter for an imaged particle based on component configurations of a system used to image the particles. In general, the size of an imaged particle may differ from dimensions of an actual particle depending on the magnification of the imaging system used to image the particle. In addition, other component configurations of an imaging system may affect the diameter as well. For example, an imperfect lens, diffraction from optical apertures, optical filter distortion, as well as several other components of an imaging system may affect and, in some cases, distort dimensions of an imaged pixel (referred to herein as the smear of the imaged particles). In some cases, the point spread function (PSF) (alternately quantified as the modulation transfer function (MTF)) of the imaging lens may be the primary contributor to distortion.

Although either set of pixels corresponding to the two peak pixels may be rejected, it may be advantageous to reject the set of pixels corresponding to the peak pixel having a lower fluorescence measurement since the characteristics of such a set of pixels may be less distinguishable versus the other set of pixels during further image processing. In some cases, the method may continue to evaluate the remaining set of pixels to determine if it is sufficient for further imaging processing. For example, the method may continue to block 74 to determine whether a rate of intensity change of an optical parameter among the set of pixels is indicative of a single particle or a clump of particles. Generally, it is desirable to reject clumps of particles due to the difficulty of obtaining accurate and distinct information for each of the particles. In yet other embodiments, the selection of the two sets of pixels for rejection in block 72 may be determined by computing the rate of intensity change of an optical parameter among the sets of pixels. In particular, upon determining the distance between the peak pixels is less than a predetermined threshold, rates of intensity change of an optical parameter may be computed for each set of pixels as an indicator of which set should be rejected. Different manners for computing a rate of intensity change among a set of pixels are outlined in blocks 76-78 and 80-82, respectively, and described in more detail below.

Since the method of particle rejection may include a combination or sequential processing of blocks 72 and 74, the flowchart in FIG. 3 includes a dotted line between blocks 72 and 74 to indicate the possibility of such a connection between the respective processes. Such a connection, however, is optional. In particular, blocks 72 and 74 may not, in some embodiments, be performed in conjunction and, therefore, the arrow between blocks 72 and 74 may be omitted. In other embodiments, the processing of blocks 74 and 72 may be reversed and, as such, the method described herein may include a connection between blocks 78 and/or 82 and block 70. In other embodiments, blocks 70 and 72 may be omitted from the method. Alternatively, block 74 (and its exemplary procedures for performing such a process outlined in blocks 76-82) may be omitted from the method. In yet other cases, the method may be configured to select the route of image processing subsequent to block 62 and, therefore, may lead to either of blocks 70 and 74 as illustrated in FIG. 3.

Referring to block 74, a rate of intensity of an optical parameter among a plurality of pixels surrounding at least one of the locations determined in block 62 may be computed. As noted above, this rate may be used to accept the particle or to reject the particle for further image data processing. More specifically, the rate may be a measure of the spatial gradient of the emission characteristics of the particle (i.e., the distribution of the fluorescence emission level) and the spatial gradient may be used to determine how isolated the particle of interest is from neighboring particles. In some embodiments, the process of block 74 may follow the sequence of steps outlined in blocks 76 and 78. In particular, the method may include computing a rate of intensity of an optical parameter for a set of pixels arranged within a predetermined radius surrounding a location determined in block 62. In some embodiments, the predetermined radius may be approximately equal to a projected diameter of the particle represented by the determined location. In other cases, the predetermined radius may be greater or less than a projected diameter of the imaged particle represented by the determined location.

After the rate of intensity change of the optical parameter is computed, the method may continue to block 78 in which the set of pixels may be accepted or rejected for further image data processing by comparing the rate of intensity to a predetermined threshold. In some embodiments, block 78 may include accepting the set of pixels for further processing upon computing the rate of intensity change is greater than or equal to a predetermined threshold. In particular, a relatively high rate of intensity change of an optical parameter may be indicative of a single particle within the set of pixels, which may be desirable for further image processing. In addition to such a process, block 78 may include rejecting the set of pixels for further processing upon computing the rate of intensity change is less than a predetermined threshold. In particular, a relatively low rate of intensity change of an optical parameter may be indicative of a clump of particles within the set of pixels, which as noted above may be undesirable for further image processing.

An alternative manner in which to compute a rate of intensity change of an optical parameter within a set of pixels is outlined in blocks 80 and 82 in FIG. 3. In particular, the method may additionally or alternatively be routed to block 80 to sum values of the optical parameter for two distinct sets of pixels respectively arranged within different predetermined radii surrounding one of the locations determined in block 62. It is noted that the radii may be adjusted to best match the particle's spread across the detector pixel array, which usually varies depending upon the point spread function (PSF) (alternately quantified as the modulation transfer function (MTF)) of the imaging lens, the position of the particle with respect to the focal plane of the imaging subsystem, and the size of the particle itself. For example, in some embodiments, it may be advantageous for one predetermined radius to be approximately equal to a projected diameter of a single particle within the image and the other predetermined radius to be approximately 1.5 times greater than a projected diameter of a single particle within the image. Other radii, however, may be used as well as different ratios of the radii may be used. It is further noted that if values of a background signal is subtracted for pixels within one radius, the background signal may also be subtracted from the values for the pixels within other radius.

Subsequent to summing the values of the optical parameter, a ratio of the summed values corresponding to each of the radii may be computed. In particular, the summed values obtained using the smaller radius may be divided by the summed values obtained using the larger radius or vice versa. In either case, the ratio may be used to accept or reject the set of pixels for further image data processing as noted in block 82. In particular, block 82 may include accepting the set of pixels for further evaluation upon determining the ratio differs from a set value by an amount less than or equal to a predetermined threshold. In addition, block 83 may include rejecting the set of pixels for further evaluation upon determining the ratio differs from the set value by an amount greater than the predetermined threshold.

The determination of the threshold may depend on a variety of factors, including but not limited to radii chosen for performing the process outlined in block 80, the size of the particles to be imaged, the smear of the particles within the image, as well as the settings of the imaging system used. Consequently, the predetermined threshold for accepting and rejecting set of pixels in block 83 may vary greatly among different applications. However, a general guideline is that a ratio closer to unity may be indicative of a set of pixels that may be desirable for further processing since there is little contribution from the pixels outside the smaller radius. In other words affects of optical parameter values from neighboring particles is likely to be minimal and, thus, the error in a value for an optical parameter of interest will be relatively small. Alternatively, if this ratio is significantly less than unity, then it is likely that a neighboring bright particle is affecting the optical parameter value of the particle of interest. In such instances, the particle of interest may be discarded, or the integration radii may have been improperly chosen. In this manner, before the image data for a particle of interest is discarded, the integrations described above may be performed with different radii.

An algorithm for performing such an additional integration may include establishing an inner diameter to outer diameter ratio for each bead at some fixed ratio (such as the 1.5×) and storing the results. In such cases, the inner diameter may be slightly larger than the expected bead projection will be, such as 1.5 times larger than the expected bead projection. Then the inner and outer diameters may be reduced slightly (keeping same ratio of as before) for each bead. Subsequent thereto, the collection of ratios may be compared to see if a majority of the ratios have changed. If most of the ratios have not changed, the inner diameter is still too big and no energy is (yet) getting outside the inner circle to the outer circle, so the inner and outer diameters need to be reduced again for each bead. Conversely, if some of the ratios have changed, it may be indicative that some energy may be moving to the outer circle.

The process may be iterated any number of times based on the distribution of the changes from the last diameter's collection of ratios. For example, if the percentage of particles that coincide is known (and, consequently, should be discarded), the percentage may be equated to a desired percentage of ratios to end the iteration. An estimation of the percentage of particles that coincide may be drawn from knowledge of how the system typically behaves from past data off the production line, or alternatively a visual examination of the test image. If the percentage of coinciding particles is unknown, the "history" of the changes step by step for an emerging percentage that changes and remains constant with decreasing inner diameter may be an indicator to terminate the iteration. As an example, given 5% of the ratios change with one reduction, then 10%, then 10% again, and 12% the fourth time. In such an example, 10% may be the number of particles that should be discarded. When the percentage of 12% was reached, the inner circle may have been too small, cutting off the smaller-single-good beads. As such, the previous diameter should be used as the stopping point. All of such process steps may be repeated with different inner/outer diameter ratios to see if a clearer trend of percentage changes emerges. In such cases, the process may include an "outer loop" in the algorithm where you start first with a larger ratio, then step through sweeping the ratio until you are actually smaller than the original one (optionally skipping the original ratio since it has already been computed).

As noted above, the method described herein for image data processing may include a process of inter-image alignment. In some embodiments, the process of inter-image alignment described herein may be performed subsequent to the determination of a level of background signal within an image and/or subsequent to discovery of particles within an image. In some cases, the process of inter-image alignment may be specifically performed subsequent to the method of background signal measurement described in reference to FIG. 2 and/or subsequent to the method of particle discovery described in reference to FIG. 3. In other embodiments, however, the process of inter-image alignment described herein may be performed independent of background signal measurement and/or particle discovery processes. In any case, the inter-image alignment process may be performed at the factory after the instrument has been assembled. In addition or alternatively, the inter-image alignment process may be performed in the field, particularly if components of the system are changed after shipment from the factory.

In general, inter-image alignment may be performed if multiple images of particles are acquired using two or more detectors, each of which may be coupled to an optical filter as described above, or if interchangeable optical filters are substituted between images taken with a single camera, since the filter itself may affect the image. The multiple images are generally taken at different wavelengths such that different levels of fluorescence may be measured and used to classify the particles. Due to the mechanical tolerances of the imaging subsystem hardware, however, spots corresponding to particles within the each of the multiple images may not be in absolute alignment in a composite of the multiple images. Such mis-registration of the spots may undesirably inhibit the ability to associate a particle's location in all channels imaged. The image-to-image registration, however, may be modified using the inter-image alignment technique described herein to better align the spots. As described below, the inter-image alignment correction process may be a simple translation of image coordinates in the x and/or y directions. In addition or alternatively, the inter-image alignment process may include rotation of one or more of the multiple images.

Figure 4:
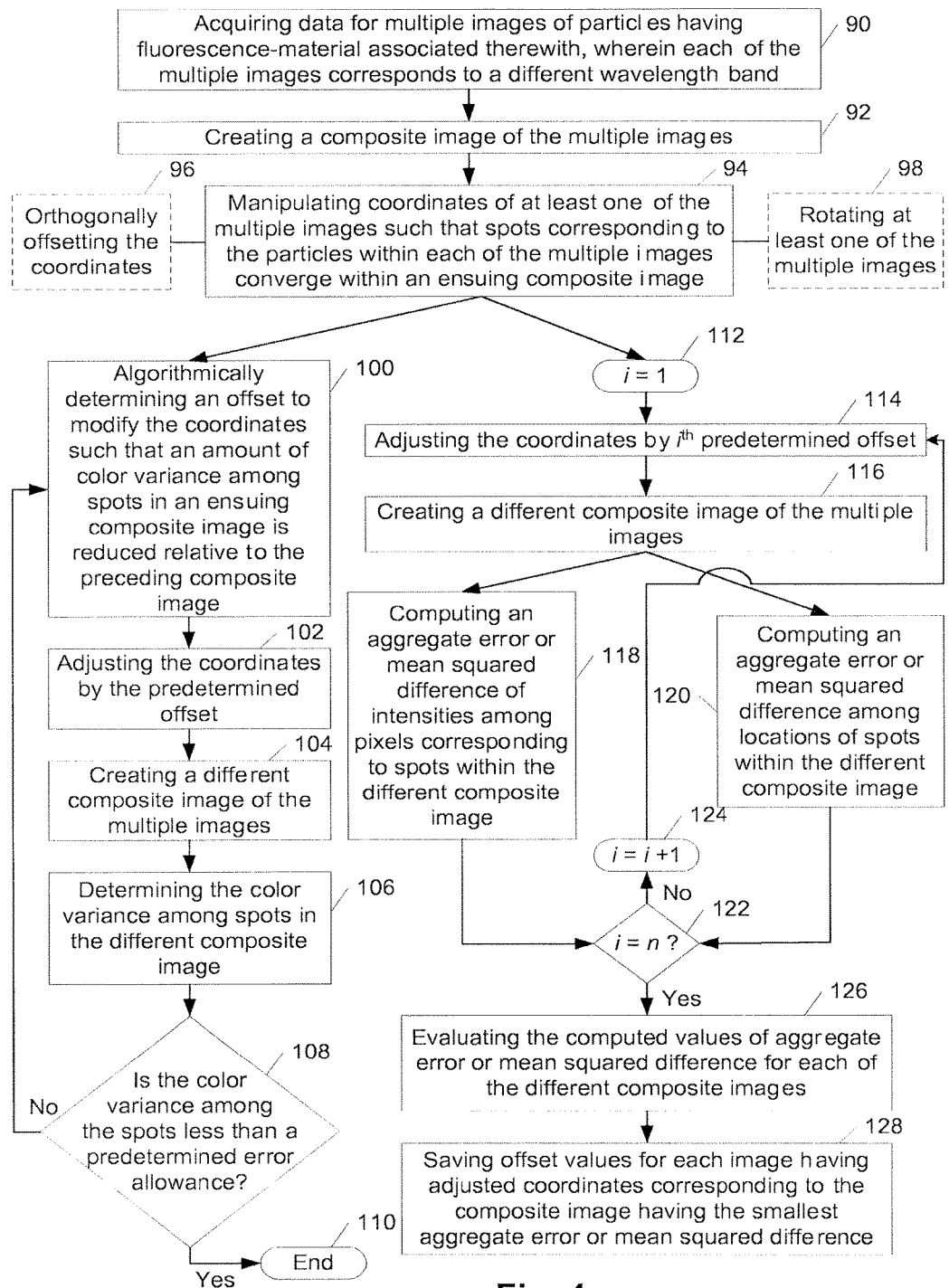
FIG. 4 is a flowchart outlining a method of inter-image alignment.

FIG. 4 illustrates a flowchart illustrating an exemplary sequence of steps for a process of inter-image alignment. As shown in block 90 of FIG. 4, the process may include acquiring data for multiple images of particles having fluorescence-material associated therewith, wherein each of the multiple images corresponds to a different wavelength band. In some cases, the data may be acquired directly from an imaging system, but in other cases, the data may be acquired from a storage medium. In either case, the data may be representative of multiple images taken at different wavelengths as noted above. Exemplary wavelengths that may be used may correspond to different color channels, such as but not limited to red for classification channel 1, green for classification channel 2, blue for the reporter channel. As further noted above, in order to accommodate each color channel, the particles used for the method described herein may be specially dyed to emit at all wavelengths or in all wavelength bands of interest. In particular, in order to measure both classification and reporter signals within the multiple images, the inter-image alignment process described herein may be performed using specially dyed particles, which not only emit fluorescence in the classification wavelength(s) or wavelength band(s), but also in the reporter wavelength or wavelength band.

After the data for the multiple images has been acquired, the method may continue to block 92 in which a composite image of the multiple images is created. In general, the composite image is a single image with the multiple images overlapped relative to each other. As noted above, due to the mechanical tolerances of the imaging subsystem hardware, spots corresponding to particles within the each of the multiple images may not be in absolute alignment in a composite of the multiple images. As such, inter-image alignment may be needed. In particular, the method may include manipulating coordinates of at least one of the multiple images such that spots corresponding to the particles within each of the multiple images converge within an ensuing composite image as noted in block 94. In some embodiments, the coordinate values of all of the multiple images but one (the one being referred to herein as the "reference image") may be manipulated. Alternatively, the coordinate values of fewer multiple images may be manipulated. In this manner, the coordinate values of images other than the reference image may be maintained for the inter-image alignment process. In some cases, the image acquired at the wavelength or wavelength band of light emitted by the reporter dye may be designated as the reference image. In other embodiments, the image acquired at a wavelength or wavelength band of light emitted by a classification dye may be designated as the reference image.

As noted above and illustrated in FIG. 4, the manipulation of the coordinates may, in some cases, include an orthogonal offset of image coordinates in the x and/or y directions as noted in block 96. In addition or alternatively, the manipulation of the coordinates may include rotation of one or more of the multiple images as noted in block 98. Blocks 96 and 98 are outlined by dotted lines, indicating either or both of the processes may be used for the manipulation of the image coordinates.

In the process of orthogonal translation, a positive or negative integer translation offset in either the x or y dimension may be determined for the manipulation of the coordinate values. The respective offsets may be added to the coordinates of one or more non-reference images, and a new composite image may be created with the multiple images, some of which having the new coordinates. In general, the orthogonal translation correction steps may be performed until no further improvement in alignment within a composite image is possible. Upon determining no further improvement by orthogonal translation may be obtained, the x translation and y translation values for each non-reference image having coordinates which were manipulated by the process may be saved for subsequent imaging of particles. Any appropriate data structure, such as a table, may be suitable for such values.

As noted above, the manipulation of the coordinate values may additionally or alternatively include rotating coordinates of one or more non-reference images. In some embodiments, the rotation process may be employed if the images are not aligned sufficiently via translation correction. In other embodiments, the rotation process may be performed prior to, instead of, or alternately with the orthogonal translation process. In yet other cases, the rotation process may be performed concurrently with the orthogonal translation process. In particular, one or more non-reference images may be rotated and one or more other non-references may be translated with orthogonal offsets for the manipulation of image coordinates. In other embodiments, coordinates of individual non-reference images may be both rotated and orthogonally offset. In any case, the range of orthogonal offsets which may be employed for the inter-image alignment process may, in some embodiments, be +/−10 pixels and the range of rotational offsets may be +/−2 degrees. Larger or smaller amounts of offsets, however, may be employed for either or both manners of manipulating the coordinates.

Regardless of the manner in which the rotation of images is incorporated relative to orthogonal offsets of image coordinates, the rotation process may generally include selecting the origin (i.e., center of rotation) to be near the midpoint of the x and y dimensions of the image (denoted as $x_{origin}$, $y_{origin}$). A new blank image buffer may be created with the same dimensions as the source image (i.e., the non-reference image to be rotated). For each pixel in the source image, a current vector from the center of rotation may be determined. In particular, the distance from the pixel of interest to center of rotation of the image may be determined from the square root of $[(x-x_{origin})^2+(y-y_{origin})^2]$, x and y being the coordinates of the pixel. In addition, the current vector's angle may be determined from the arctangent of the $y_{distance}$ divided by the $x_{distance}$ and adding or subtracting a quadrant-dependent modifier from the value of the arctangent to adjust the angle per quadrant. In such cases, $y_{distance}$ is the distance along the y-axis between $y_{origin}$ and the pixel of interest and $x_{distance}$ is the distance along the x-axis between $x_{origin}$ and the pixel of interest.

Subsequent to the aforementioned computations, a constant user defined "adjustment" angle may be added to the current pixel's vector to determine the angle by which to rotate the pixel. The new location for the pixels (e.g., in x and y coordinates) may be determined by the following equations:

new x coordinate=square root of $[(x-x_{origin})^2+(y-y_{origin})^2]$*cos(rotated angle)+$x_{origin}$+ $x_{translation}$ (if applicable)+0.5    (1)

new y coordinate=square root of $[(x-x_{origin})^2+(y-y_{origin})^2]$*sin(rotated angle)+$y_{origin}$+ $y_{translation}$ (if applicable)+0.5    (2)

The value of the pixel under consideration may be copied to the blank image buffer's pixel at the new x and y coordinates. After non-reference images intended for rotation have been processed, a new composite pseudo-color image may be recreated. In general, the steps outlined above for the rotation process may be repeated to minimize the color variance across each non-reference image. The final rotation values may be saved for each non-reference image in a suitable data structure such as an adjustment table for subsequent imaging.

In general, the iteration of coordinate manipulation described above in reference to block 94 may be conducted in reference to a number of different parameters. For instance, the iteration of coordinate manipulation may depend on the amount of color variance among spots of a composite image, aggregate error or mean square difference of intensities among pixels corresponding to spots of a composite image, and/or aggregate error or mean square difference of locations of spots within a composite image. An outline of each of such techniques is outlined in blocks 100-128 in FIG. 4 and described in more detail below.

In particular, block 100 includes a process of algorithmically determining (i.e., by means of an algorithm) an offset to modify coordinates of at least one of the multiple images such that an amount of color variance among the spots in an ensuing composite image is reduced relative to a preceding composite image. The color variance in the composite image is generally induced by misalignment of at least one of the multiple images. For example, in embodiments in which red, green, and blue channels are used for the respective multiple images, the converged color of a spot corresponding to a particle in a composite image is expected to be white. Alignment variations of the multiple images, however, may cause spots on the individual images corresponding to one or more of the red, green, and blue channels to be offset relative to each other. As a consequence, the individual colors in the composite image may extend beyond an edge of the white spot, inducing a variance of color at the spot. It is noted that the formation of a white spot in a composite image is a result of the combination of the images produced by the red, green, and blue channels, but the method described herein is not necessarily limited to making images with such channels. In particular, any number of multiple images may be formed by several different color channels and, consequently, the method described herein is not restricted to the formation of three images or the color channels of red, green, and blue.

As described above and outlined in block 102 of FIG. 4, the misalignment of the images may be reduced by adjusting the coordinates of one or more of the multiple images by predetermined offsets. Such predetermined offsets may include orthogonal offsets and/or rotational offsets as described above in reference to blocks 96 and 98. Subsequent to block 102, a different composite image of the multiple images including the predetermined offsets may be created as noted in block 104. The method may continue to block 106 in which the color variance among the spots in the newly created composite image is determined. As noted in decision block 108, blocks 100-106 may be repeated in embodiments in which the color variance is greater than (and/or equal to) a predetermined error allowance for particular offset amount. Conversely, the method of inter-image alignment may terminate at block 110 in embodiments in which the color variance is less than (and/or equal to) the predetermined error allowance. In general, the predetermined error allowance set for block 108 may depend on the accuracy desired for the composite image as well as the offset amount and, therefore, may vary among applications.

Techniques for the iteration of coordinate manipulation based on aggregate error or mean square difference of pixel intensities and/or locations of spots within a composite image are described in reference to blocks 112-128 in FIG. 4. In particular, both techniques may start at block 112 at which i is set equal to 1. Such a designation is used to reference the $1^{st}$ of several predetermined offsets to adjust the coordinates of at least one of the multiple images as noted in block 114. In some embodiments, the selection of predetermined offsets through which the processes are iterated may be specific to the parameter by which alignment in the composite image is measured (i.e., by aggregate error or mean square difference of pixel intensities or locations of spots within a composite image). In other embodiments, the selection of predetermined offsets may be independent of the technique used. In either case, the processes may continue to block 116 to create a different composite image of the multiple images including the predetermined offsets. Thereafter, processes specific to the techniques may be employed. For example, the method may continue to block 118 to determine an aggregate error or mean squared difference in intensities among the pixels of the composite image created in block 116. Alternatively, the method may continue to block 120 to determine an aggregate error or mean squared difference in locations of spots within the composite image created in block 116.

In either case, a determination may be subsequently made at block 122 as to whether i equals n, n being the number of predetermined offsets by which to adjust the coordinates of the multiple images. In cases in which i does not equal n, the method may continue to block 124 to increase the value of i by one and the processes outlined in blocks 114-120 may be repeated. Upon determining i equals n, the method may continue to block 126 in which the computed values of aggregate error or mean square differences for each of the different composite images are evaluated. In particular, the computed values of aggregate error or mean square differences for each of the different composite images may be evaluated to identify the offset (i.e., the translation and/or rotation) values that resulted in the minimum error for a composite image. The identified offset values may be saved for each non-reference image for which coordinates were adjusted as noted in block 128. Any appropriate data structure, such as a table, may be suitable for such values. In both of the above described embodiments, the identified offset values may be applied to the coordinate systems of classification images created during subsequent images. In particular, the classification images may be translated and/or rotated directly into new image buffers using the equations described above and the original classification image buffers may then be discarded.

Inter-image particle correlation may be performed after the image coordinate systems are aligned. In particular, after the image coordinate systems are aligned, actual particles may be discarded by position, assuming that more than one classification image is acquired at more than one wavelength or wavelength band. Simply stated, if a particle is not present across all classification images, it may be eliminated from further processing.

In one example, using each classification image's particle collection previously identified using the particle discovery method described above and the translation/rotation values for each classification image, the best matching particle that lies within a given radius may be identified. Identifying the best matching particle may include creating a nested series of n loops, each level of which represents a classification image, for iterating through each collection of particles. At the deepest nesting level, the method may include determining if the particle's adjusted coordinates from all outer loops lie within a given radius. The coordinates at each nesting level may be translated according to the alignment table and equations described above for inter-image alignment before the distance is determined. If the distance is less than a given radius, the innermost loop's particle location may be temporarily stored for later comparison against other matches at the innermost level. If the distance of the second particle at the innermost level is less than that of a previously found particle, the temporarily stored particle location may be replaced with the present distance. If not, the method may be continued for the next particle. At the end of the iteration of the second from outermost loop, the temporary location of the best match to the outermost location may be stored to a collection. If there are no matches within a given radius for the outer loop particle, then the instance of the particle is automatically eliminated from further consideration as the output of the correlation algorithm is the collection created above.

To speed up the overall process, if there is a match identified as described above, the particle may be identified as "already used" in each subsequent loop such that processing time is not expended to consider it again. The images may also be separated into a number of subsections, and each subsection may be correlated separately to reduce processing time. In such an instance, the number of subsections is preferably selected such that the total savings in loop iterations is not lost in the time it takes to decompose the image into sections. In addition, to avoid loss of comparison capability at the boundaries of the subsections, the regions may have a slight overlap. Furthermore, if the regions are overlapped, the degree to which regions overlap may be selected to reduce the potential to duplicate particles at the overlap.

The method may also include fluorescence integration of reporter fluorescence emission. Since the reporter emission level is not constant and is an unknown, it is not possible or necessary to use the particle discovery technique employed for the classification images to identify the pixels in the reporter image that are used in the integration. Instead, the fluorescence at the same x and y coordinates of the particles found in the classification images may be used.

In one such example, using the translation and rotation values from the adjustment table determined by the inter-image correlation, each discovered particle may be mapped to the appropriate coordinates of the reporter image. For the starting location of each particle, the coordinate system from the non-adjusted reference classification image may be used. The translation x and y values and rotation angle that were determined for the reporter represent the direction an imaged particle in the reporter image may be moved to thereby coincide with the location of the particle in the classification reference image. However, the transformation that is performed here involves translating the reference coordinate system to the reporter coordinate system. The x and y translation values can be "converted" by simply inverting the sign of each adjustment parameter (negative values become positive and vice versa). Similarly, the sign of the rotation angle may also be inverted before the reporter coordinate is found. After the signs of all parameters are inverted, the equations described above for the inter-image alignment step may be used to identify the center of integration. The integral of all reporter pixels that lie within the given integration radius may be determined.

As noted above, the method described herein for image data processing may include a process of image plane normalization. Ideally, an imaging system is evenly illuminated to prevent position dependent emission variance among particles. In reality, however, each spot on the imaging field has a given illumination level. In addition, the fluorescence bandpass filter(s) and the imaging lens or lenses used within the system may not transmit the same amount of light for all points in the image. In order to compensate for such variations across the image, a normalization method or algorithm may be applied to the measured values of optical parameters. In some embodiments, the process of image plane normalization described herein may be performed subsequent to one or more of the process described above, particularly with regard to those described in reference to FIGS. 2-4. In other embodiments, however, the image plane normalization described herein may be performed independent one or more of such processes.

Figure 5:
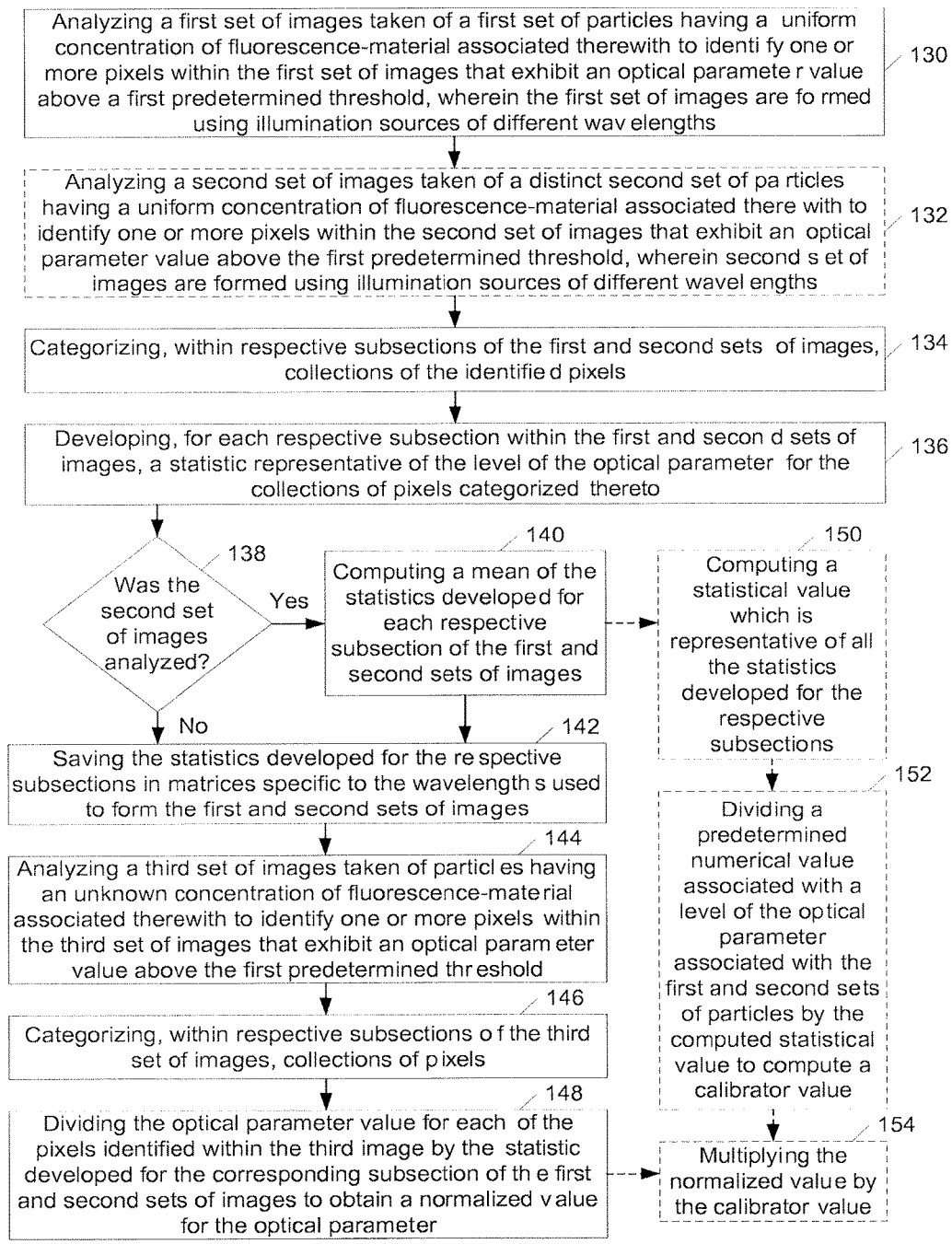
FIG. 5 is a flowchart outlining a method for creating a normalization matrix for a imaging system and applying the normalization matrix for subsequent imaging.

FIG. 5 illustrates a flowchart illustrating an exemplary sequence of steps for a process of image plane normalization. As shown in block 130 of FIG. 5, the process may include analyzing a first set of images taken of a first set of particles having a uniform concentration of fluorescence-material associated therewith to identify one or more pixels within the first set of images that exhibit an optical parameter value above a first predetermined threshold. The first set of images may include any number of images, including a single image or a plurality of images. In embodiments in which a plurality of images are taken, the first set of images are formed using illumination sources of different wavelengths, such as but limited to wavelengths corresponding to red, green, and blue channels.

In some cases, the method may optionally (as indicated by the dotted line border) include block 132 in which a second set of images taken of a second distinct set of particles having a uniform concentration of fluorescence-material associated therewith is analyzed to identify one or more pixels within the second set of images that exhibit an optical parameter value above a first predetermined threshold. As with the first set of images, the second set of images may include any number of images and, in cases in which a plurality of images are taken, the plurality of images may be formed using illumination sources of different wavelengths. In some embodiments, analyzing a second set of images taken for a different set of particles with known concentrations may be advantageous for reducing the effects of noise and particle non-uniformity among the statistics subsequently developed for respective subsections of the first and second sets of images. In particular, the effects of noise and particle non-uniformity may be reduced by taking a mean of the optical parameter values measured for each of the respective subsections of the first and second sets of images as described below in reference to block 140.

Regardless of whether the method includes analyzing the second set of images, the method may continue to block 134 to categorize, within respective subsections of the first set of images and in some cases the second set of images, collections of the pixels identified in the processes described in reference to blocks 130 and 132. In particular, the sets of images may be separated into an array of subsections and collections or conglomerates of contiguously arranged pixels may be arranged within the subsections based upon their location within the image. More specifically, for each particle that is identified, the subsection within the first and second sets of images to which it belongs may be determined. The array of subsections may include any number of rows and columns, depending on the clarity of desired background signal, the processing capability of the system, and/or the number of particles being analyzed. As further shown in FIG. 5, the method may continue to block 136 to develop, for each respective subsection of the first set of images and, in some cases, the second set of images, a single statistic representative of the level of the optical parameter for the collections of pixels categorized thereto. In general, the statistic may be selected from any number of statistical parameters, including but not limited to median, mean, mode, and trimmed mean. In some embodiments, determining a median value may be particularly advantageous.

As noted by decision block 138 in FIG. 5, the method may continue to block 140 in embodiments in which two sets of images taken for two distinct sets of particles are analyzed. Block 140 specifies that a mean of the statistics developed for each respective subsection of the first and second sets of images is computed. Following block 140 or upon determining that only one set of images are analyzed for the categorization of pixel collections in block 138, the method may continue to block 142 to save the statistics developed for the respective subsections in matrices specific to the wavelengths used to form the first and second sets of images. Such matrices are used to compute normalized values for optical parameters measured for image particles having an unknown concentration of fluorescence-material associated therewith as further described below in reference to block 148.

In particular, the method may include block 144 for analyzing a third set of images taken of particles having an unknown concentration of fluorescence-material associated therewith to identify one or more pixels within the third set of images that exhibit an optical parameter value above the first predetermined threshold. As with the first set of images, the third set of images may include any number of images and, in cases in which a plurality of images are taken, the plurality of images may be formed using illumination sources of different wavelengths. The method may continue to block 146 in which a collections of pixels identified in block 144 are categorized into respective subsections of the third set of images. In order to compensate for position dependent emission variances among the particles having unknown concentrations of fluorescence material, normalized values for the measured optical parameters may be computed.

In particular, block 148 outlines that the optical parameter value for each of the pixels identified within the image may be divided by the statistic developed for the corresponding subsection of the first and second sets of images to obtain a normalized value for the optical parameter.

In some embodiments, the resultant normalization value for each identified pixel may be multiplied by a single "calibrator" value to adjust its final calibrated value relative to an external standard. The calibrator value may be determined from the normalization matrix as described above for a substantially uniform set of particles of known concentration. In particular, the method may optionally include (as noted by the dotted line borders) block 150 for computing a statistical value which is representative of all of the statistics developed for the respective subsections of one or both of the first and second sets of images. The statistical value may be selected from any number of statistical parameters, including but not limited to median, mean, mode, and trimmed mean. In some embodiments, determining a median value may be particularly advantageous. The determination of the calibration value may further include dividing a predetermined numerical value associated with a level of the optical parameter associated with the different sets of particles having uniform concentrations of fluorescence-material associated therewith by the computed statistical value as noted in block 152. As noted above and in block 154 in FIG. 5 the calibrator value may be multiplied by a normalized value obtained for an optical parameter of a particle having an unknown concentration to adjust its value to an external standard.

It is noted that the normalizing and calibrating techniques described above are not limited to normalizing each pixel in all images. Rather, the normalizing and calibrating techniques may be applied particles identified within an image. Such a process may be particularly advantageous for minimizing calculations versus applications specific to normalizing and calibrating pixels.

It will be appreciated to those skilled in the art having the benefit of this disclosure that this invention is believed to provide computer-implemented methods, storage mediums, and systems for image data processing. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system, comprising:
    an imaging subsystem configured to image, at different wavelength bands, particles disposed within the imaging subsystem, wherein the imaging comprises:
        selecting a first set of one or more optical filters corresponding to a first wavelength band;
        illuminating the particles through the first set of optical filters;
        selecting a second set of one or more optical filters corresponding to a second wavelength band; and
        illuminating the particles through the second set of optical filters; and
    a data processing subsystem configured to:
        store data acquired for multiple images of the particles, and wherein particular images of the multiple images include spots corresponding to the particles, wherein a first image of the particular images corresponds to the first set of optical filters, wherein a second image of the particular images corresponds to the second set of optical filters;
        create a first composite image of the multiple images, wherein the first composite image includes first composite spots corresponding to the particles, the first composite spots having a first amount of misalignment from the spots in the particular images; and
        modify coordinates of at least one of the multiple images such that a second composite image based on the modified coordinates includes second composite spots having a second, smaller amount of misalignment from the spots in the multiple images.

2. The system of claim 1, wherein the first set of optical filters corresponds to a plurality of wavelength bands including the first wavelength band.

3. The system of claim 1, wherein illuminating the particles through the first set of optical filters comprises directing a first light source at the first set of optical filters, and wherein illuminating the particles through the second set of optical filters comprises directing a second light source at the second set of optical filters, and wherein the first light source is not directed at the second set of optical filters.

4. The system of claim 3, wherein the first light source is configured to emit light having different wavelength band characteristics than the second light source.

5. The system of claim 1, wherein the modifying includes determining an offset such that an amount of color variance in the second composite image is less than an amount of color variance in the first composite image.

6. The system of claim 5, wherein the data processing subsystem is further configured to iteratively create a series of composite images until a particular one of the series of composite images has a color variance below a threshold color variance.

7. The system of claim 1, wherein the modifying includes:
    based on a plurality of predetermined offsets, determining an aggregate error or a mean squared difference among pixels corresponding to the particles within the first composite image; and
    selecting a predetermined offset by minimizing the aggregate error or mean squared difference.

8. The system of claim 1, wherein the data processing subsystem is further configured to iteratively create a plurality of composite images until a threshold amount of misalignment is reached.

9. A method, comprising:
    a computing system receiving data corresponding to multiple images of a plurality of particles, wherein the multiple images correspond to different wavelength bands, wherein particular images of the multiple images include spots corresponding to individual ones of the plurality of particles, wherein a first image of the particular images corresponds to a first set of one or more optical filters, and wherein a second image of the particular images corresponds to a second set of one or more optical filters;
    the computing system creating a first composite image based on the multiple images, wherein the first composite image includes first composite spots corresponding to the particles, the first composite spots having a first amount of misalignment from the spots in the particular images;
    the computing system modifying coordinates of at least one of the multiple images such that a second composite image based on the modified coordinates includes second composite spots having a second, smaller amount of misalignment from the spots in the multiple images; and
    the computing system outputting the second composite image.

10. The method of claim 9, wherein the particles include fluorescent material, and wherein the images are based on fluorescence from the fluorescent material.

11. The method of claim 10, wherein the particles include at least two fluorescent materials.

12. The method of claim 9, wherein the particles include at least one of: a microparticle, a nanoparticle, a quantum dot, a cell, a polystyrene bead, or a latex bead.

13. The method of claim 9, wherein at least some of the particles emit light in a classification wavelength band.

14. The method of claim 13, wherein the at least some of the particles also emit light in a reporter wavelength band.

15. An article of manufacture including a computer-readable medium having instructions coded thereon that, in response to execution by a computing system, cause the computing system to carry out operations comprising:
    acquiring data corresponding to multiple images of a plurality of particles, wherein the multiple images correspond to different wavelength bands, wherein particular images of the multiple images include spots corresponding to individual ones of the plurality of particles, wherein a first image of the particular images corresponds to a first set of one or more optical filters, and wherein a second image of the particular images corresponds to a second set of one or more optical filters;

creating a first composite image based on the multiple images, wherein the first composite image includes first composite spots corresponding to the particles, the first composite spots having a first amount of misalignment from the spots in the particular images; and modifying coordinates of at least one of the multiple images such that a second composite image based on the modified coordinates includes second composite spots having a second, smaller amount of misalignment from the spots in the multiple images.

16. The article of claim 15, wherein the operations further comprise:

determining whether a selected particle that has been imaged at a first wavelength band has also been imaged at a second wavelength band;

in response to determining that the selected particle has been imaged at the second wavelength band, accepting the selected particle for further evaluation; and in response to determining that the selected particle has not been imaged at the second wavelength band, rejecting the selected particle for further evaluation.

17. The article of claim 15, wherein the modifying includes performing an orthogonal offset of the coordinates, performing a rotation of the at least one of the multiple images, or both.

18. The article of claim 15, wherein the modifying includes modifying coordinates of all of the multiple images except for one reference image.

19. The article of claim 18, wherein the reference image is based on fluorescence from a classification dye.

20. The article of claim 15, wherein the modifying is based on a color variance among the first composite spots, and wherein the modifying is repeated until the color variance is less than a threshold color variance.

* * * * *